United States Patent [19]

Guirguis

[11] Patent Number: 5,024,237
[45] Date of Patent: Jun. 18, 1991

[54] MODULAR FLUID SAMPLE PREPARATION ASSEMBLY

[75] Inventor: Raouf A. Guirguis, Rockville, Md.

[73] Assignee: La Mina Ltd., British Virgin Isls.

[21] Appl. No.: 369,610

[22] Filed: Jun. 21, 1989

Related U.S. Application Data

[63] Continuation-in-part of Ser. No. 308,763, Jan. 10, 1989, Pat. No. 4,961,432.

[51] Int. Cl.$^5$ ............................................. A61B 5/00
[52] U.S. Cl. .................................... 128/760; 604/317
[58] Field of Search ...................... 128/760, 761, 771; 604/317, 318, 403, 404; 422/102

[56] References Cited

U.S. PATENT DOCUMENTS

| | | | |
|---|---|---|---|
| 3,312,221 | 4/1967 | Overment | 604/317 |
| 3,777,739 | 12/1973 | Raitto | 128/2 |
| 3,881,465 | 5/1975 | Raitto | 128/2 |
| 4,040,791 | 8/1977 | Kuntz | 23/259 |
| 4,042,337 | 8/1977 | Griffith | 23/259 |
| 4,084,937 | 4/1978 | Beach | 23/259 |
| 4,244,920 | 1/1981 | Manschot et al. | 422/102 |
| 4,473,530 | 9/1984 | Villa-Real | 128/762 |
| 4,492,258 | 1/1985 | Lichtenstein et al. | 128/761 |
| 4,557,274 | 12/1985 | Cawood | 128/760 |
| 4,573,983 | 3/1986 | Annis | 604/322 |
| 4,661,100 | 4/1987 | Rechsteiner | 604/317 |
| 4,685,472 | 8/1987 | Muto | 128/760 |
| 4,700,714 | 10/1987 | Fuisz | 128/767 |
| 4,741,346 | 5/1988 | Wong et al. | 128/760 |

Primary Examiner—Max Hindenburg
Attorney, Agent, or Firm—Gipple & Hale

[57] ABSTRACT

An apparatus for collecting and testing biological molecular indicators in a biological fluid comprising a tubular container having an open end, and a compartmentalized container holding beads with immobilized ligands. The biological fluid namely urine is collected in the tubular container and is forced to flow through the sample compartmentalized container so that predetermined molecules of opposite matching charges to immobilized ligands become attached to the bead ligands for easy color testing to obtain specified medical tests.

23 Claims, 9 Drawing Sheets

MODULAR FLUID SAMPLE PREPARATION ASSEMBLY

RELATED CASES

This application is a continuation-in-part application of U.S. patent application Ser. No. 07/308,763 filed Jan. 10, 1989, U.S. Pat. No. 4,961,432.

BACKGROUND OF THE INVENTION

The present invention is directed to medical and laboratory specimen collecting and testing equipment, and more specifically to an apparatus for detecting the presence of specific antigens in biological fluids.

It is generally necessary in diagnosing and testing for many diseases to collect biological fluids from a patient, e.g., sputum, blood, pleural and peritoneal cavity fluids, urine, etc. for analysis. It is important during the collection handling of biological fluid specimens that the potential of specimen contamination and the spread of any infection from the specimen be minimized. In addition there is also the potential for specimen damage during the collection and/or shipment process as well as the potential for destruction of certain components of the specimen because the packaging does not screen particulants in the fluids or collects and holds different fluid components which will negate the test results or result in false data being obtained when the specimen is tested.

It has been noted that one of the problems in collecting biological fluid specimens occurs not only during the collection of the specimens but also in the transport or shipment of the specimens after collection to the laboratory for analysis.

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial in connection with the cap and allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

One such specimen collection device shown by U.S. Pat. No. 4,040,791 discloses a collection receptacle having a nipple upon which is mounted a specimen container which receives a predetermined amount of the specimen in a sealed condition. The specimen container is provided with an integally formed cap which is placed over the opening in which the collector nipple is inserted. U S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

It is therefore desirable to provide an easy to handle apparatus which uses a fluid sample such as urine and separates various antibodies from urine so that testing can be performed quickly and accurately with minimum time.

It is thus an object of the invention, particularly where antigens are being removed from the body fluids for a variety of tests to detect and visually indicate specific antigens in the body fluid samples. Previously such testing has been accomplished by a series of tests involving a number of different containers and expensive laboratory equipment. Mass testing using such a series of tests is expensive, time consuming, and often unsatisfactory.

BRIEF SUMMARY OF THE INVENTION

The invention is directed toward a body fluid preferably an antigen analysis device. This device is in the form of a modular sample container in the housing, which can be washed or treated with biological fluids allowing the fluid sample to be quickly analyzed. The primary antibody (against the antigen) is included in the sample prior to the addition of the sample. This antibody will be provided prelabelled with coloring reagents. The testing sample is added to the container where the antigen reacts with the antibody to form antigen-antibody complex. If there is an absence of the antigen in the specimen sample the antibody will remain unoccupied. The beads housing unit contains two different sets of beads, one with antigen covalently(irreversible) bound, and the other without the antigen to act as a control. On the top of the housing unit, a circular (disk) membrane is mounted with a immobilized secondary antibody against the primary antibody. The disk membrane provides the surface upon which the test result is visualized.

In the accompanying drawings, there is shown an illustrative embodiment of the invention from which these and other of objectives, novel features and advantages will be readily apparent.

DETAILED DESCRIPTION OF THE INVENTION

The preferred embodiment and best mode of the invention is seen in FIGS. 1 through 12. The invention shown in the drawings comprises a modular fluid sample container with sample collection apparatus. While the invention can be used for any body fluid such as sputum, blood, body fluids or urine, it is primarily designed for use in collecting urine/blood samples for use in testing for the presence of various kinds of cancer in the body.

Figure 1:
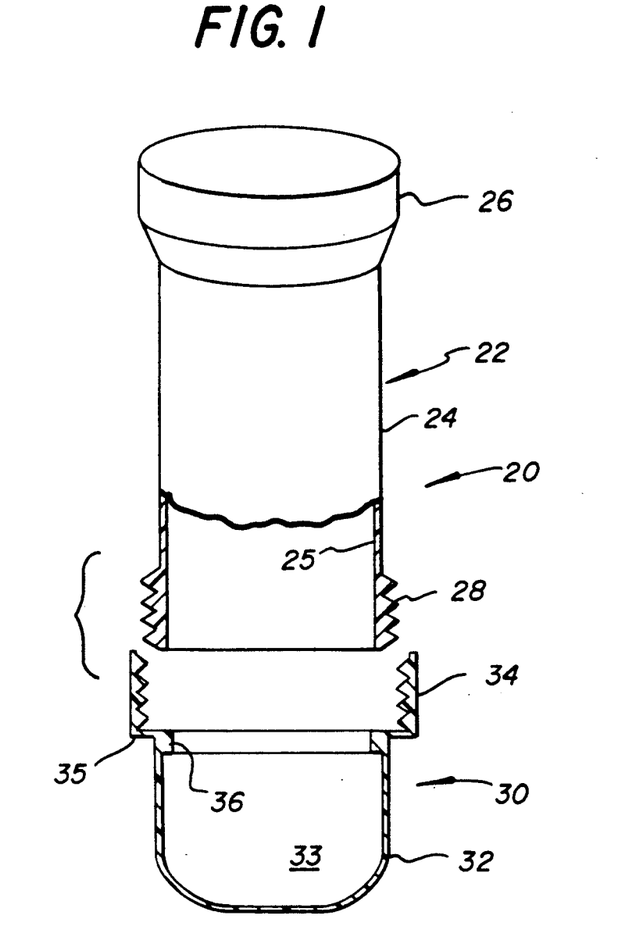
FIG. 1 is a cross sectional view of separated units of the sample collection apparatus of the invention.
Figure 2:
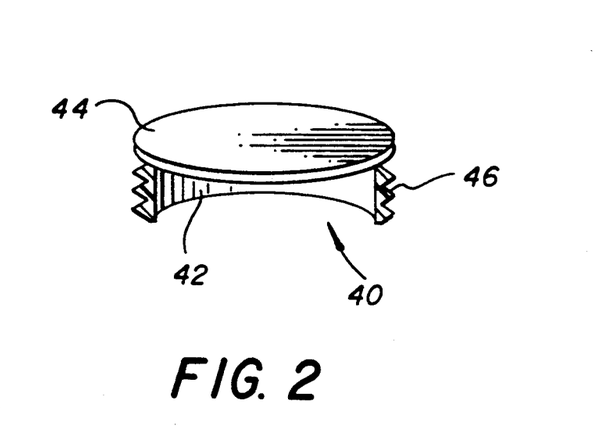
FIG. 2 is a cross sectional view of a cap for the shuttle storage unit of the sample collection apparatus of FIG. 1.
Figure 3:
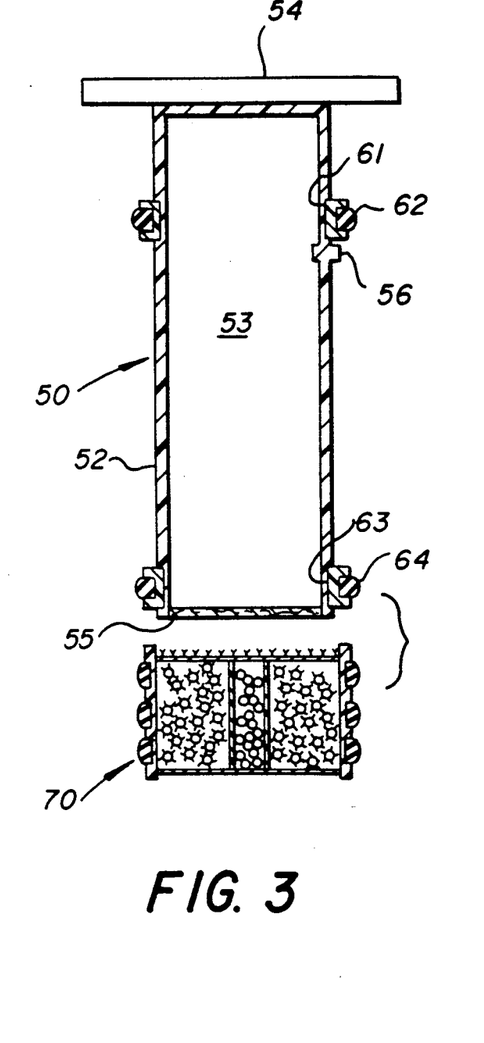
FIG. 3 is an exploded cross sectional view of the piston assembly and sample/test container of the shuttle apparatus which fits into the sample collection apparatus of FIG. 1.
Figure 4:
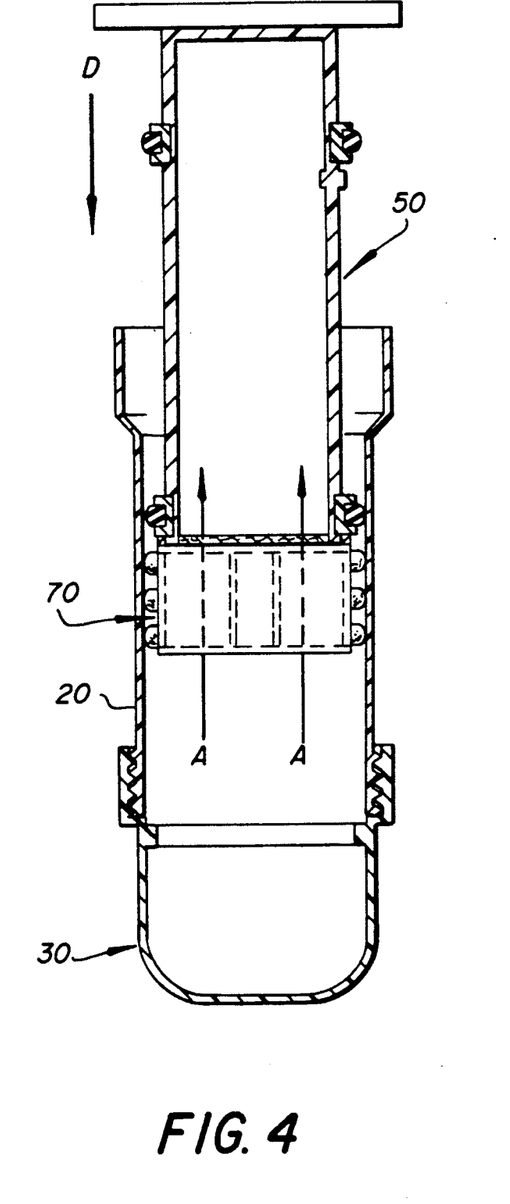
FIG. 4 is a cross sectional view of a sample filtration purification shuttle apparatus with direction of movement of the plunger shown by arrow D' and direction of flow of the fluid shown by arrows A.
Figure 5:
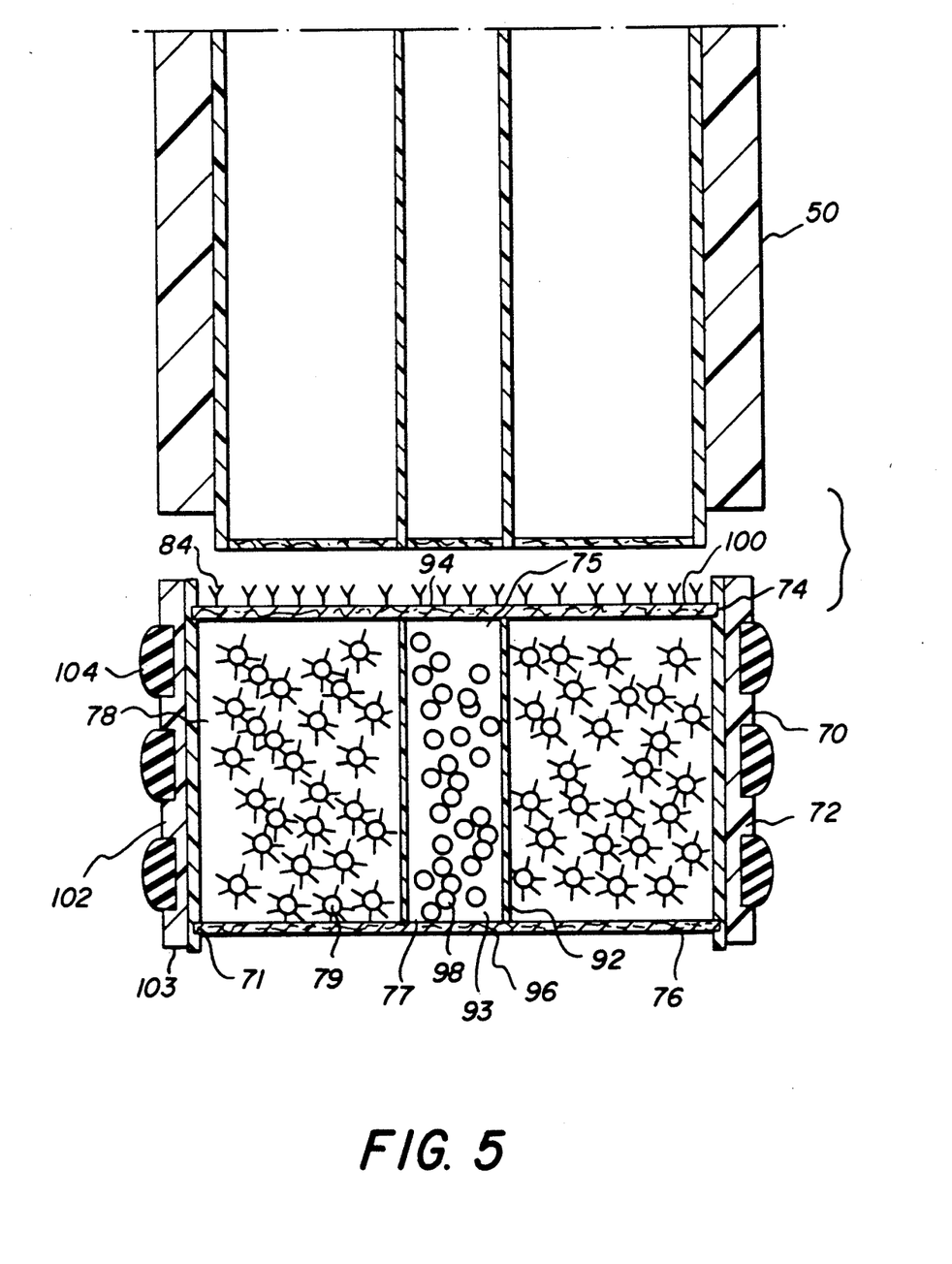
FIG. 5 is an exploded enlarged cross sectional view of the end of the piston assembly and sample test container.
Figure 6:
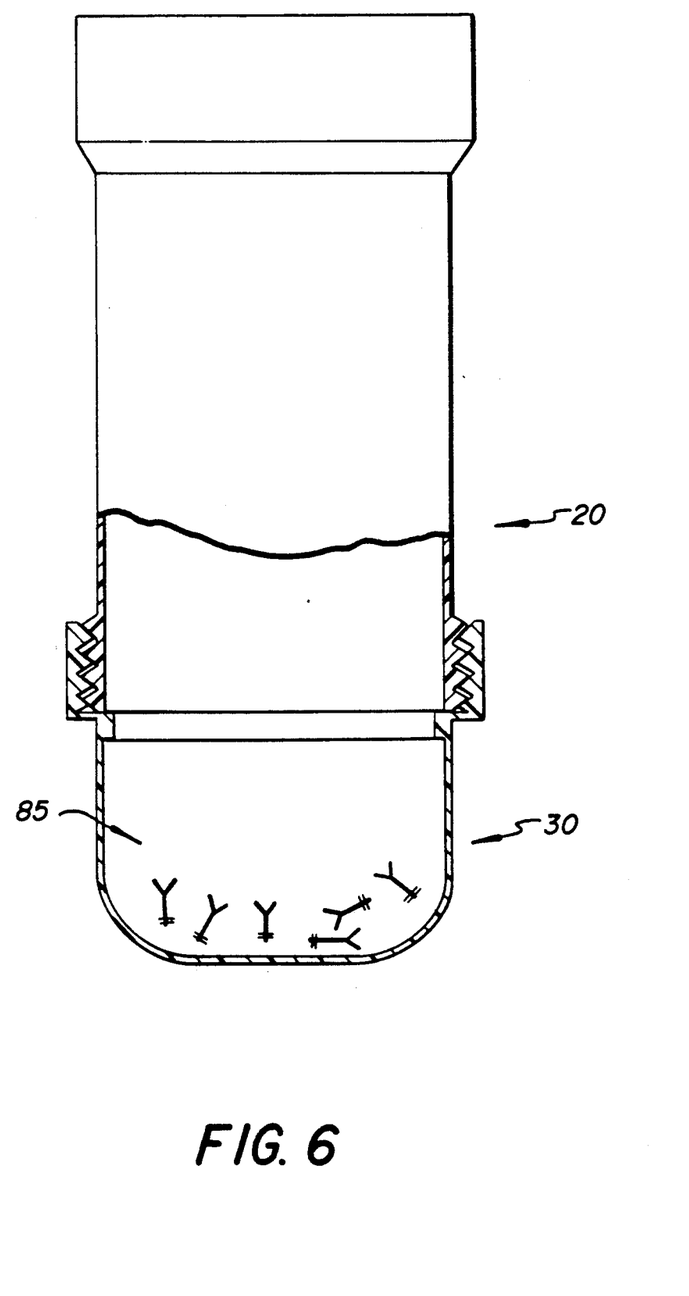
FIG. 6 is an enlarged cross sectional view of the sample collecting apparatus with labelled primary antibodies.
Figure 7:
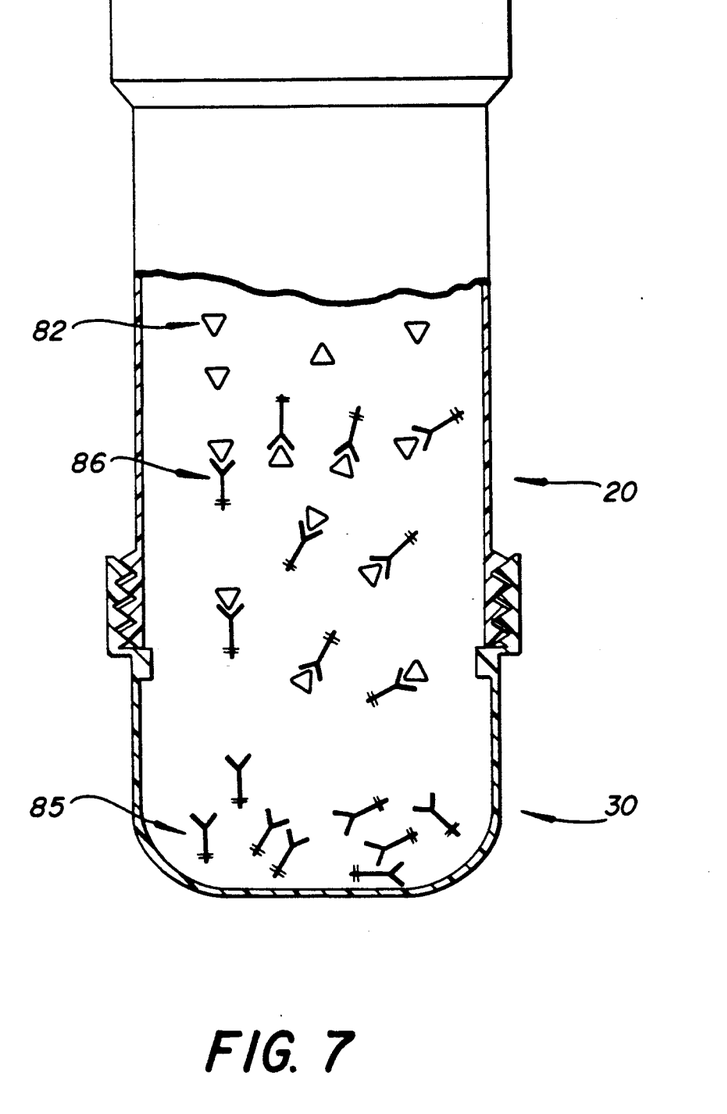
FIG. 7 is an enlarged cross sectional view of the sample collection apparatus with labelled primary antibodies, antigen antibody complexes and antigen.
Figure 8:
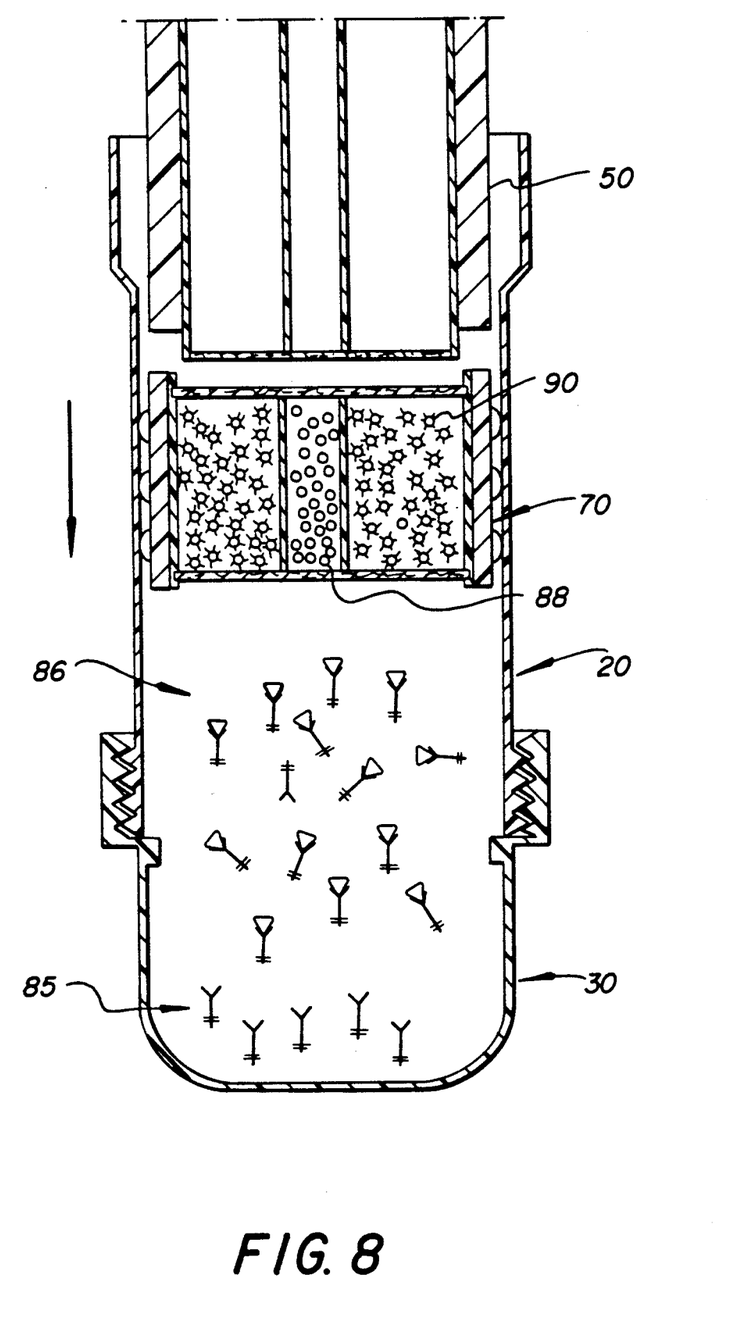
FIG. 8 is a cross sectional view of the sample collection apparatus holding labelled primarY antibodies, antigen antibody complexes with the sample test container inserted and plunger about to engage the sample test container.
Figure 9:
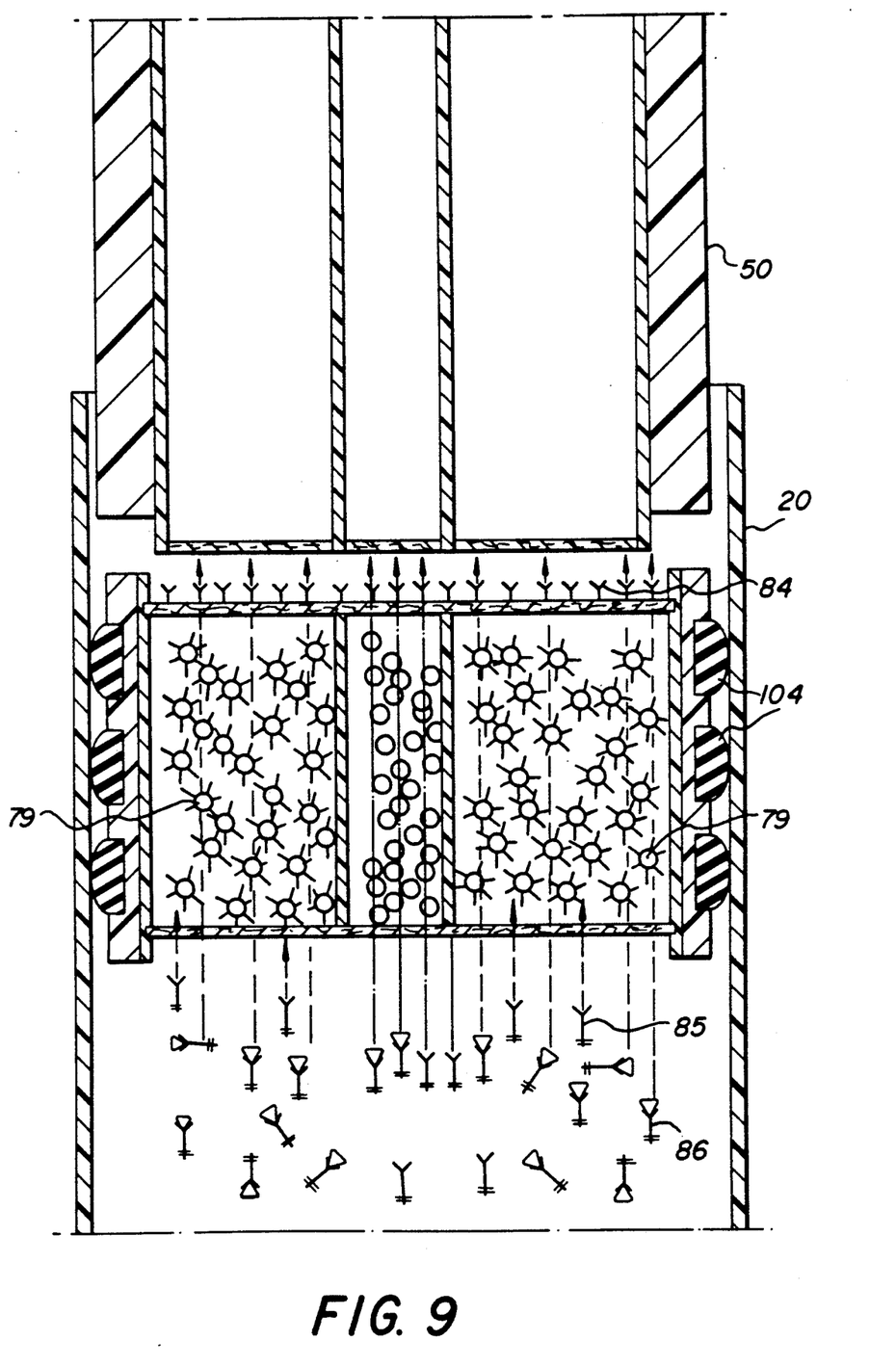
FIG. 9 is an enlarged cross sectional schematic when antigen is present.
Figure 10:
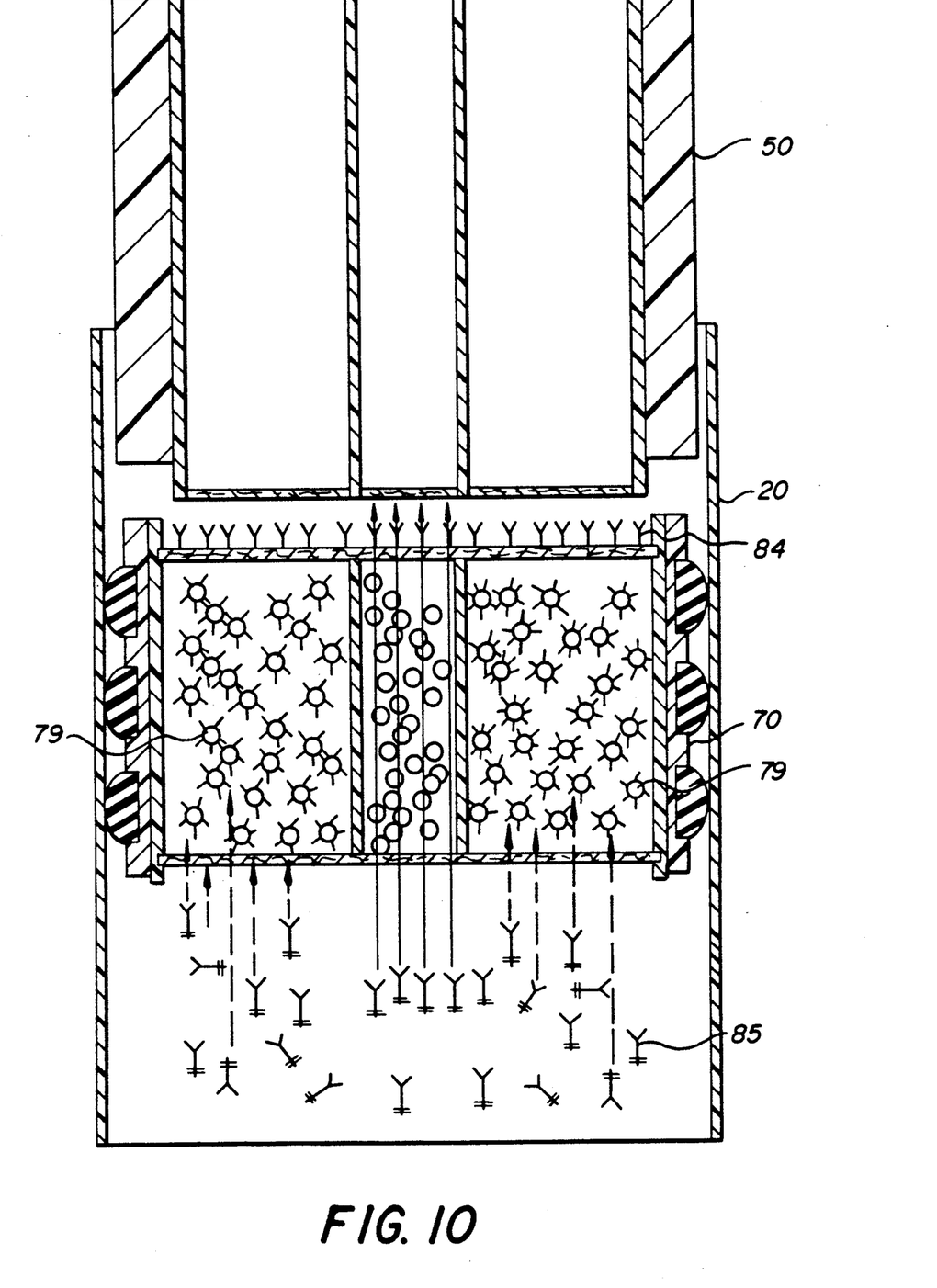
FIG. 10 is an enlarged cross sectional schematic when antigen is absent.
Figure 11:
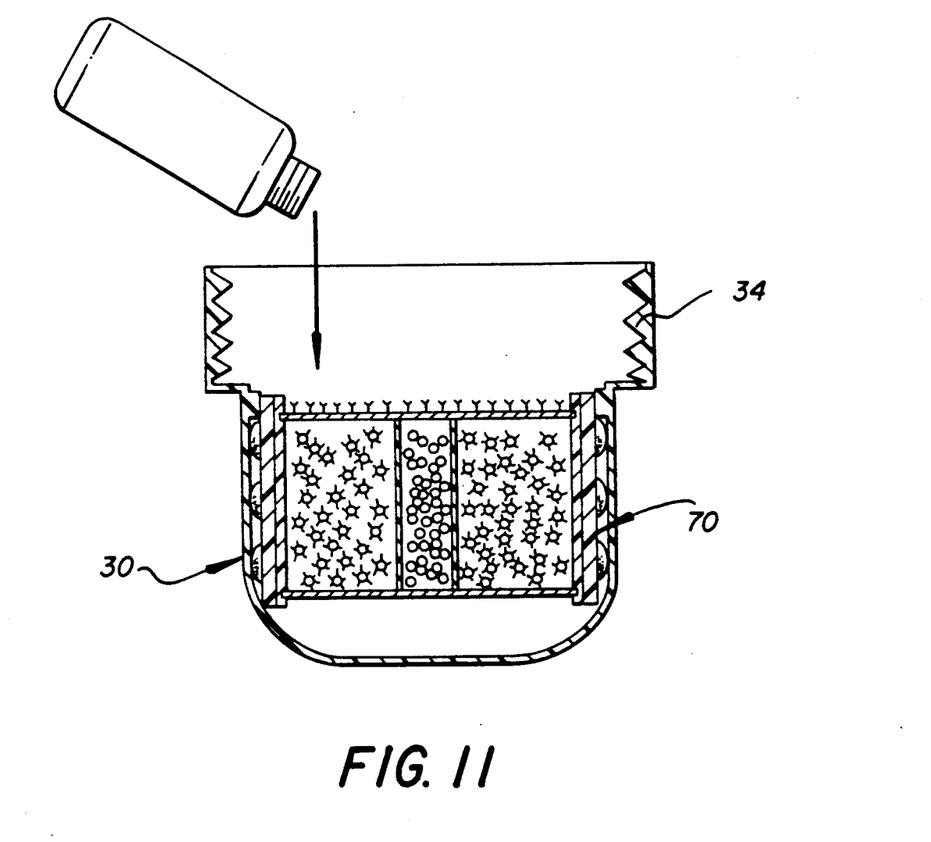
FIG. 11 is a schematic representation of the addition of color developing solution to the sample test container which is shown in cross section.

As shown in FIGS. 1 through 3, a sample collection apparatus 20 is constructed of polystyrene and comprises a tubular collection unit 22, a shuttle storage unit 30 and an associated cap member 40. The tubular collection unit 22 is constructed with a tubular open ended cylindrical body 24 having formed on one end an open flared end portion 26 and on the other end a threaded portion 28. The flared end portion 26 has a wide mouth to more easily receive body fluid which is loaded into the unit and also prevents entrapment of air between the resin container unit 70 and the surface of the sample fluid. The shuttle storage unit 30 is removably secured to the threaded portion 28. The shuttle storage unit 30 comprises a cylindrical cup shaped body 32 with a stepped female threaded open end 34 and shoulder 35. The open end 34 has a greater diameter than the diameter of body 32. A stop member 36 comprised of a circular ring or integrally formed rib is formed or secured to the inner surface of the shuttle body 32 immediately below the shoulder 35 of the threaded stepped open end 34. This stop member 36 serves as a stop for a transporter or shuttle assembly 50 shown in FIG. 3 which will be discussed later on in the specification. The cap member 40 as shown in FIG. 2 is formed with a cylindrical body 42 having a lid or cover 44 and external threads 46 which mate with the female threaded end portion 34 of the shuttle body 32. Thus the shuttle storage unit 30 and cap 40 can be used to form a closed container holding the particulants testing material or fluid as desired. It should also be noted that a threaded or snug fitting cap (not shown) can be placed over end portion 26 so that the sample collection apparatus can be closed.

The transporter assembly 50 as shown in FIG. 3 is designed to fit within cylindrical body 24 and slideably move along the interior wall surface 25 in a sealed relationship and abut a shuttle sample container 70 for deposit within the shuttle storage body 32. The transporter assembly 50 is constructed of a transparent plastic comprising a hollow cylindrical piston body 52 provided with a thumb cover 54 and a bottom end member 55. An air release aperture 56 is formed in the piston body so that there is communication between the interior chamber 53 of the piston body into the outside atmosphere. The bottom end member 55 is porous and allows fluid flow therethrough into the interior chamber 53 as the exterior rigid surface engages the outer surface of the container 70. Mounted around the piston body in annular channels 61 and 63 cut into the exterior surface of the body 52 are respectively an upper O-ring 62 and lower O-ring 64. These O-rings slideably engage and form a fluid seal against the interior surface 25 of sample collection unit 22. The shuttle sample container 70 is adapted to receive end member 55 within the upper inner wall surface of the container cylindrical body 72 and has a diameter or size sufficient to allow it to be seated within the interior 33 of shuttle storage unit 30.

The shuttle sample container 70 as clearly shown in FIGS. 3, 5 and 8-10 is constructed with a cylindrical body 72 open at both ends and threaded on the outside to allow the mounting of a porous circular top cover 74 which is threaded on the inside of the cylindrical body 72 and defines a central aperture 75. A circular disc membrane 100 preferably between 0.20-0.5 microns in thickness is positioned on the outer surface of top cover 74. This membrane has an outer surface which is coated with immobilized secondary antibody 84 by means which are well known in the art. A circular bottom cover 76 with a central aperture 77 is threaded on the inside of cylindrical skirt 71 on the other end of body 72. The body 72, top cover 74 and bottom cover 76 define a chamber 78 which is filled with beads with immobilized antigen 79. Positioned inside the central apertures 75 and 77 and engaging the top and bottom covers 74 and 76 is a tubular cylindrical bead module 90. The tubular module 90 comprises a cylindrical body 92 defining a chamber 93 and an end walls 94 and 96 formed with porous septums to allow easy flow through of the fluids. Cylinder chamber 93 is filled with beads not having the antigen 98 which acts as a control.

An O-ring sleeve 102 comprising a plurality of O-rings 104 is mounted to the exterior surface of the cylinder 72. The tubular module 90 and container 70 may be filled with sample beads of all forms and sizes which can be specifically manufactured for ion exchange. Since the pH versus the net charge curve is a unique characteristic of a molecule and provides the basis for the selectivity of ion exchange and chromatofocusing, beads can be tailored to attract specific biomolecules. Ion exchange chromatography is a high resolution technique which separates biomolecules on the basis of their charge properties. Biomolecules interact with an ion exchanger by electrostatic forces, and since nearly all biomolecules exist in a charged state, the charged groups on the surface of the biomolecule interact with groups of opposite charge on the ion exchanger.

Suitable beads for ion exchange are manufactured under the trademark TOYOPEARL now marketed as: DEAE-, CM-, and SP-TOYOPEARL having a swelled state particle size in 20-50 $\mu$m, 40-90 $\mu$m, and 60-150 $\mu$m. Other suitable ion exchange beads are marketed by Pharmacia under the tradenames: Mono Q (interacts with net negatively charged molecules which are separated by selective salt elution: anion exchange); Mono S (interacts with net positively charged molecules which are separated by selective salt elution: cation exchange); and Mono P, an anion exchanger for separating molecules (interacts with net negatively charged molecules which are separated in a pH gradient according to their isoelectric points (chromatofocusing). Mono Q and Mono S beads are strong ion exchangers in the pH range 2-12. The definition of a strong ion exchanger is one which shows no variation in ion exchange capacity (e.g. mmoles Cl bound per ml of gel) with a change in pH. It does not have the ability to take up or lose protons with changing pH i.e. it has no buffering capacity. Sample properties of such ion exhcangers are that sample loading capacity does not decrease at high or low pH values due to loss of charge from the ion exchanger as the charge characteristics do not change with changes in pH and there exists a simple mechanism of interaction between the media and the solute due to the absence of intermediate forms of charge interaction allowing high resolution with fast flow rates and large sample loads. A weak ion exchanger's ionic capacity changes with pH and therefore shows buffering capacity. Thus Monobeads show a stability of the matrix throughout the pH range 2-12 and the non-denaturing pore structure (>500 Å)of the matrix is important for retaining biological activity and immunological reactivitY associated with the biomolecules. The large pore diameters provide high loading capacities and fast kinetics for large biomolecules because the molecules can move freely in and out of the interior of the matrix. Furthermore Monobeads are based on a hydrophilic, polymeric resin which has minimal non specific binding effects.

The beads can also have high affinity chromatography or hydrophobicity (e.g. phenylsepharose beads). The chemical and mechanical stability of the support (resin) and its linkage to the ligand (antigen) play a key role in affinity chromatography. Preferably the module bead chambers hold high affinity resin beads with specific antibodies or antigens immobilized onto the solid phase resin (e.g. Actigel-ALD, Protein A, Protein G . . . etc.) so that antigens in the sample can bind to their specific antibodies, or alternately the antibody complexes can become bound while passing through the resin module and become immobilized as well. The principle of affinity chromatography requires that a successful separation of a biospecific ligand is available and that it can be chemically immobilized to a chromatographic bed material, the matrix. Numbers of methods well known in the art have been used to couple or immobilize the antigen to a variety of activated resins. Examples of immobilization techniques which exhibit variable linkage are those formed by the reaction of the reactive groups on the support with amino, thiol, hydroxyl, and carboxyl groups on the protein ligand. The immobilized ligand must also retain its specific binding affinity for the substance of interest with the bound substances being selectively desorbed in an active form. The selection of the ligand is influenced by two factors. First, the ligand should exhibit specific and reversible binding affinity for the substance to be purified and secondly it should have chemically modifiable groups which allow it to be attached to the matrix without destroying its binding activity.(Examples of such are Protein G Sepharose manufactured by Pharmacia, Hydrazide AvidGel Ax manufactured by BioProbe International, and Actigel-ALD manufactured by Sterogene Bioseparation Inc.)

In the case of Actigel-ALD a monomonic, stable, low reactively aldehyde group is introcuded to the support through 5 atoms hydrophilic spacer arm. This establishes well defined, stable secondary amine linkages without side reaction or the release of hydrophobic or reactive leaving groups. Another advantage to the use of Actigel-ALD is that it does not cross link proteins therfore allowing proteins to retain high bioactivity after their immobilization. Actigel-ALO SUPER FLOW also available from Sterogene Bioseparation Inc. permits a linear flow rate of up to 3000 cm/h which would fit nicely with the flow rates in the device (approx 10-100 cm/min).

Visual affinity chromatography can be obtained through the use of color markers in the form of dye affinity chromatography product are available and are manufactured by TosoHaas under the designation TSK-GEL TOYOPEARL DYE AFFINITY CHROMATOGRAPHY PRODUCTS made with TOYOPEARL HW-65 as the base matrix and Cibacron Blue F3GA or reactive red 120 as the dye reagent. Blue-TOYOPEARL 650 and Red-TOYOPEARL 650 have differing protein binding capacities.

FIGS. 7-12 show the sample collection apparatus containing a urine sample having particulate matter therein with a transporter assembly 50 and associated resin/sample container 70 mounted therein. As the shuttle resin/sample container 70 and its associated O-rings 104 is mounted in the interior of the sample collection unit 22, adjacent surface 25, piston 52 is pushed down in the direction shown by arrow D causing the urine to pass through the bottom cover wall 76 which filters the urine, chambers 78 and 93, holding the respective beads and top cover wall 74 and membrane 100 into the chamber 53. It should be noted that the air contained in chamber 53 is pushed out by the fluid through air release aperture 56 into a chamber formed by the concentric outer surface of the piston body 52 and the inner surface 25 of sample collection unit 22. The shuttle resin/sample container 70 is pushed down until it enters into the body cavity 33 at which time the lower O-ring 64 engages stop rib 36 thus seating the shuttle resin/sample container 70 in a predetermined position so that it cannot break or damage the shuttle storage unit 30. When the shuttle resin/sample container 70 is seated in the shuttle storage unit 30, the upper "O" ring 62 becomes engaged with the inner surface 25 of cylindrical body 24. This will discontinue the communication between the body cavity 53 and the atmosphere through the air release aperture 56. Consequently the fluid entering the body cavity 53 will be trapped inside it even after removal of the shuttle storage unit 30 together with the seated resin/sample container 70. It will also be noted that the particulate matter which has been screened by cover wall 76 is thus concentrated in the bottom of chamber 33.

Figure 12:
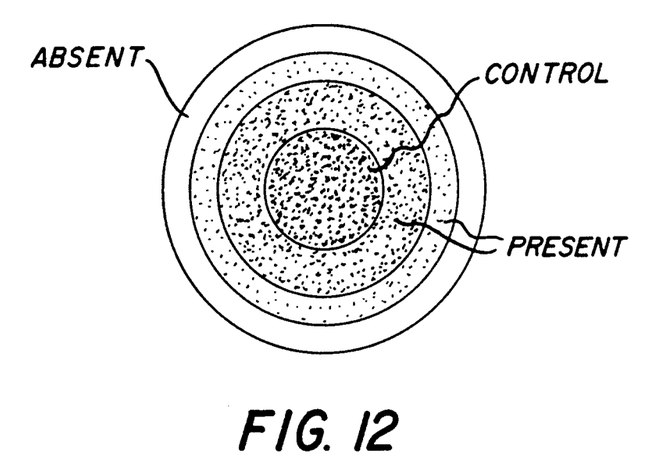
FIG. 12 is a top plan view of the top surface of the sample test container membrane showing different coloration test zones.

The resin bead material with matrix and primary ligand (in this case antigen) having had flow contact with the fluid namely urine, captures through antigen-antibody reaction or immune reaction the specific component of the fluid which is to be tested; in this example, the primary antibody. The primary antibody 85 (against the antigen 82) is included in the sample prior to the addition of the sample. This antibody will be provided prelabelled with coloring reagents. A buffering reagent is also provided with the sample container to optimize the antigen antibody reaction. (e.g. pH 8) since the urine pH is usually acidic. The testing sample is added to the container where the antigen reacts with the antibody to form antigen-antibody complexes 86. If there is an absence of the antigen in the specimen sample the antibody will remain unoccupied and will react with the antigen immobilized on beads. On the other hand, if the antigen is present, anitgen-antibody complexes 86 will be formed. The beads housing unit contains two different sets of beads, one set 79 with antigen covalently (irreversible) bound, and the other set 98 without the antigen to act as a control. On the top of the beads housing, there is a circular (disk) membrane with a immobilized secondary antibody 84 against the primary antibody. The upper surface of the disk membrane 100 provides the surface upon which the antibody and/or antigen-antibody complexes are captured and the test result is visualized. The shuttle storage unit 30 is unscrewed from the tubular collection unit 22 with the shuttle resin/sample container 70 contained therein, the transporter assembly 50 remaining with the tubular collection unit 22 and cap 40 is screwed on threaded end 34 to keep the sample in a secured contained condition after adding the proper preservatives for analysis of the particulate matter or for testing by pouring color developing solution to visualize the prelabeled antibody captured on the top surface of the circular disk (membrane). The degree of color developed as shown in FIG. 12 should correlate with the amount of prelabeled antibody/antigen complexes which in turn correlates with the amount of antigen present in the sample. Furthermore, the center of the circular disk should represent the maximum positive response (color) that can develop if the prelabeled antibody were to pass through the second set of beads 98 with no antigen bound. This positive control should reflect the current state of the coloring reagents as well as the prelabeled antibody at the time the test is performed.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. An apparatus for collecting molecular specimens from biological fluids comprising a tubular container; a specimen collection storage unit removably mounted in said tubular container, said specimen collection storage unit comprising a container divided into at least two separate testing compartments, a first test means with a predetermined antigen bound thereto positioned in one testing compartment and a control test means without said predetermined antigen positioned in another of said testing compartments; and membrane means mounted to said collection storage unit to visually indicate the presence of specific molecular specimens.

2. An apparatus for collecting molecular specimens from biological fluids comprising a tubular container; a specimen collection unit mounted in said tubular container, said specimen collection unit comprising a housing divided into at least two separate compartments, bead means with covalently bound antigen positioned in one of said compartments and control bead means without antigen located in another of said compartments; and a membrane mounted to said collection storage unit with immobilized secondary antibody against the primary antibody secured to said membrane to visually indicate the presence of specific molecular specimens.

3. An apparatus as claimed in claim 1 wherein said membrane means is a membrane with immobilized secondary antibodies connected thereto.

4. An apparatus as claimed in claim 1 wherein said specimen collection storage unit comprises a cylindrical housing, said housing being provided with porous end walls, said membrane means being mounted to one of said end walls, divider means dividing said cylindrical housing into a plurality of compartments, said control test means comprising control bead means mounted in one of said compartments and said first test means comprising bead means with immobilized antigen mounted in another of said compartments isolated from said control bead means.

5. An apparatus as claimed in claim 4 wherein said control bead means developes maximum color as contrasted to other coloring.

6. An apparatus as claimed in claim 4 wherein "O" ring means are mounted to the outside of said cylindrical housing.

7. An apparatus as claimed in claim 6 wherein said "O" ring means comprises a sleeve with a plurality of concentric "O" rings integrally formed on said sleeve.

8. An apparatus as claimed in claim 3 wherein said membrane ranges from 0.2 to 0.5 microns in thickness.

9. An apparatus for collecting biological fluids and holding a predetermined sample for testing comprising a tubular container having open ends; a collection storage unit removably secured to one of said container ends, said collection storage unit having an open end and a closed end, a shuttle assembly slidably mounted in said tubular container, said shuttle assembly comprising a cylindrical hollow piston defining a chamber, a top cover covering one end of said piston, "O" ring means mounted on the exterior surface of said piston to form a fluid tight seal between said "O" ring means and the interior surface of said tubular container, and sample container means removably secured to said piston and adapted to be seated in said collection storage unit, said sample container means comprising a container divided into at least two separate bead means containing compartments, bead means with an immobilized biological indicator bound thereto positioned in one said compartments and control bead means without said biological indicator located in another of said compartments; and test means mounted to said collection storage unit to visually present testing results.

10. An apparatus for collecting molecular samples from biological fluids comprising a first container means; a sample collection storage unit removably mounted to said first container means, said sample collection storage unit comprising a container divided into at least two separate bead containing compartments, bead means with a first immobilized ligand positioned in one said compartments and bead means with a second immobilized ligand located in another of said compartments; and test means mounted to said collection storage unit to visually indicate the presence of specific molecular bodies.

11. An apparatus as claimed in claim 10 wherein said bead means have capacity for cation exchange.

12. An apparatus as claimed in claim 10 wherein said bead means have high affinity chromatography.

13. An apparatus as claimed in claim 10 wherein said bead means have hydrophobicity characteristics.

14. An apparatus as claimed in claim 10 wherein said bead means are phenylsepharose.

15. An apparatus as claimed in claim 10 wherein said bead means have a capacity to bind antibodies thereto.

16. An apparatus as claimed in claim 10 wherein said bead means have a capacity to bind antigens thereto.

17. An apparatus as claimed in claim 10 wherein said bead means have a capacity to bind antigen-antibody complexes thereto.

18. An apparatus as claimed in claim 10 wherein said bead means have capacity for anion exchange.

19. An apparatus for collecting biological fluids comprising a tubular container having open ends; a collection storage unit removably secured to one of said container ends, said collection storage unit defining an open end and a closed end, stop means secured to said collection storage unit, a shuttle assembly slidably mounted in said tubular container, said shuttle assembly comprising a cylindrical hollow piston defining a chamber, a top cover covering one end of said piston, "O" ring means mounted on the exterior surface of said piston cylinder to form a fluid tight seal between said "O" ring means and the interior surface of said elongated tubular container, and sample container means removably secured to said piston, said sample container means comprising an open ended cylindrical housing, cover plate means covering each open end of said cylindrical housing, each cover plate means allowing flow of fluids therethrough, and membrane means with ligand means bound therethrough extending across the cylindrical housing suitable to attract a charged molecule of a specific determination.

20. An apparatus as claimed in claim 19 wherein said membrane means comprises a membrane ranging from 0.2 to 0.5 microns in thickness.

21. An apparatus for collecting predetermined molecules from biological fluids comprising a tubular container having open ends; a collection storage unit removably secured to one of said container ends, said collection storage unit defining an open end, stop means secured to said collection storage unit, a shuttle assembly slidably mounted in said tubular container, said shuttle assembly comprising a cylindrical hollow piston defining a chamber, a top cover covering one end of said piston, fluid flow means covering the second end of said piston, and sample container means removably mounted to said fluid flow means, said fluid flow means comprising an end member which communicates with said piston chamber, "O" ring means mounted on the exterior surface of said piston cylinder to form a fluid tight seal between said "O" ring means and the interior surface of said tubular container, said sample container means comprising a housing with means allowing fluid flow therethrough, means dividing said housing into separated sections containing a plurality of beads provided with immobilized ligand means, and membrane means extending across the cylindrical housing, said membrane means having test means secured thereto.

22. A method of testing for predetermined molecular bodies in a urine specimen comprising the steps of:
  a. collecting urine into an apparatus for collecting biological fluids comprising an elongated tubular apparatus having a flared open end;
  b. depositing a shuttle assembly into said collecting apparatus, said shuttle assembly comprising a cylindrical hollow piston defining a chamber, a top cover covering one end of said piston and fluid flow means covering the second end of said piston, and a sample container removably mounted to said piston, said sample container defining a plurality of separated chambers containing bead means;
  c. moving the shuttle assembly along the tubular container forcing urine to flow through separated chambers of the sample container into the piston chamber;
  d. removing the piston and the elongated tubular container from the sample container; and
  e. pouring color developing solution onto the sample container to obtain a test result.

23. A method of testing for predetermined molecules in urine comprising the steps of:
  a. collecting urine into an apparatus for collecting biological fluids;
  b. depositing a test container means into said collecting apparatus, said test container means having a plurality of separated chambers containing bead means with different biological indicators;
  c. transporting urine to flow through the test container's separated chambers to contact said bead means with different biological indicators: and
  d. pouring a solution onto the sample container to obtain marking indicia in respect to said bead means denoting an ascertainable test result.

* * * * *